(12) United States Patent
Oddo et al.

(10) Patent No.: US 11,123,505 B2
(45) Date of Patent: Sep. 21, 2021

(54) BREATHING APPARATUS WITH BREATH DETECTION SOFTWARE

(71) Applicant: Aires Medical LLC, Ann Arbor, MI (US)

(72) Inventors: Nicholas Leonard Oddo, Hilton Head Island, SC (US); Shane Woody, Mooresville, NC (US); Chad Josey, Mooresville, NC (US); Dylan Moore, Mooresville, NC (US)

(73) Assignee: Aires Medical LLC, Ann Arbor, MI (US)

( * ) Notice: Subject to any disclaimer, the term of this patent is extended or adjusted under 35 U.S.C. 154(b) by 0 days.

(21) Appl. No.: 16/996,063

(22) Filed: Aug. 18, 2020

(65) Prior Publication Data

US 2021/0038840 A1 Feb. 11, 2021

Related U.S. Application Data

(63) Continuation-in-part of application No. 16/704,413, filed on Dec. 5, 2019.
(Continued)

(51) Int. Cl.
*A61M 16/00* (2006.01)

(52) U.S. Cl.
CPC ...... *A61M 16/0003* (2014.02); *A61M 16/024* (2017.08); *A61M 16/026* (2017.08);
(Continued)

(58) Field of Classification Search
CPC .............. A61M 16/00; A61M 16/0003; A61M 16/0057; A61M 16/0066; A61M 16/0069;
(Continued)

(56) References Cited

U.S. PATENT DOCUMENTS 2,692,609 A 10/1954 Carter
2,972,345 A 2/1961 Spigel
(Continued)

FOREIGN PATENT DOCUMENTS

WO WO2019IB52329 A1 9/2019

OTHER PUBLICATIONS

Matthew M. Gangidine et al., "System Design Verification for Closed Loop Control of Oxygenation With Concentrator Integration", Military Medicine, vol. 181, p. 177-183, May 2016.

*Primary Examiner* — Joseph D. Boecker
(74) *Attorney, Agent, or Firm* — Caldwell Intellectual Property Law, LLC (57) ABSTRACT

A breathing apparatus includes a flow outlet airline in fluid communication with the tubing and breath detection software. The flow outlet airline includes an airline outlet, and the flow outlet airline is configured to supply an output gas to a user via the airline outlet. The breathing apparatus further includes a breath detection airline including an airline inlet. The breath detection airline is configured to receive breathing gas from the user during exhalation by the user via the airline inlet. The breathing apparatus further includes a pressure sensor in direct fluid communication with the breath detection airline. The pressure sensor is configured to measure breathing pressure from the user and to generate sensor pressure data indicative of breathing by the user. The controller is programmed to predict the breathing by the user based on the sensor breathing data received from the pressure sensor.

7 Claims, 6 Drawing Sheets

Related U.S. Application Data (60) Provisional application No. 63/047,742, filed on Jul. 2, 2020, provisional application No. 62/775,733, filed on Dec. 5, 2018.

(52) U.S. Cl.
CPC .............. *A61M 2016/0027* (2013.01); *A61M 2016/0042* (2013.01); *A61M 2205/502* (2013.01); *A61M 2230/205* (2013.01)

(58) Field of Classification Search
CPC .............. A61M 16/024; A61M 16/026; A61M 16/101; A61M 16/201; A61M 16/202; A61M 16/204; A61M 2016/0021; A61M 2016/0027
See application file for complete search history.

(56) References Cited

U.S. PATENT DOCUMENTS

| | | | |
|---|---|---|---|
| 4,044,763 A * | 8/1977 | Bird | A61M 16/00 128/204.26 |
| 4,957,107 A | 9/1990 | Sipin | |
| 5,518,526 A | 5/1996 | Baksh et al. | |
| 5,918,597 A | 7/1999 | Jones et al. | |
| 6,484,721 B1 | 11/2002 | Bliss | |
| 9,097,361 B1 | 8/2015 | Ratner | |
| 9,724,017 B2 | 8/2017 | Baloa Welzien et al. | |
| 10,046,134 B2 | 8/2018 | DeVries et al. | |
| 10,226,201 B2 | 3/2019 | Ahmad et al. | |
| 10,245,406 B2 | 4/2019 | DeVries et al. | |
| 10,265,486 B2 | 4/2019 | Allum et al. | |
| 10,315,002 B2 | 6/2019 | DeVries et al. | |
| 2002/0053345 A1 | 5/2002 | Jafari et al. | |
| 2004/0211422 A1* | 10/2004 | Arcilla | F16K 31/082 128/204.19 |
| 2005/0103346 A1 | 5/2005 | Noble | |
| 2007/0000494 A1* | 1/2007 | Banner | G16H 40/63 128/204.23 |
| 2007/0027375 A1* | 2/2007 | Melker | A61B 5/0836 600/340 |
| 2007/0125377 A1 | 6/2007 | Heinonen et al. | |
| 2008/0121232 A1 | 5/2008 | Cewers | |
| 2009/0078256 A1* | 3/2009 | Armitstead | A61M 16/024 128/204.23 |
| 2009/0199855 A1 | 8/2009 | Davenport | |
| 2010/0078024 A1* | 4/2010 | Andrieux | A61M 16/1015 128/204.21 |
| 2012/0065533 A1 | 3/2012 | Carrillo, Jr. et al. | |
| 2013/0136638 A1 | 5/2013 | Foerster | |
| 2013/0206144 A1 | 8/2013 | Ahmad | |
| 2014/0261426 A1 | 9/2014 | Ahmad et al. | |
| 2014/0283833 A1* | 9/2014 | Zheng | A61M 16/0003 128/204.22 |
| 2014/0346380 A1 | 11/2014 | Bourqui | |
| 2015/0273174 A1 | 10/2015 | Hart et al. | |
| 2015/0328417 A1 | 11/2015 | Loser et al. | |
| 2016/0193438 A1 | 7/2016 | White et al. | |
| 2017/0119279 A1 | 5/2017 | Ahmad et al. | |
| 2017/0119280 A1 | 5/2017 | Ahmad et al. | |
| 2017/0143932 A1 | 5/2017 | McCarthy et al. | |
| 2017/0224251 A1 | 8/2017 | Ahmad et al. | |
| 2017/0319800 A1 | 11/2017 | Richards | |
| 2018/0001042 A1* | 1/2018 | Albanese | A61M 16/026 |
| 2018/0071468 A1* | 3/2018 | Dennis | A61M 16/208 |
| 2018/0221608 A1* | 8/2018 | Schwaibold | A61M 16/024 |
| 2019/0217030 A1* | 7/2019 | Burgess | A61B 5/087 |
| 2019/0261891 A1 | 8/2019 | Ahmad et al. | |
| 2020/0139072 A1 | 5/2020 | Zapol et al. | |
| 2020/0188615 A1 | 6/2020 | Troili | |
| 2020/0368482 A1 | 11/2020 | Westfall et al. | |

\* cited by examiner

BREATHING APPARATUS WITH BREATH DETECTION SOFTWARE

CROSS-REFERENCE TO RELATED APPLICATIONS

This application claims priority, and the benefit of, U.S. Provisional Patent Application 63/047,742, filed Jul. 2, 2020, U.S. patent application Ser. No. 16/704,413, filed on Dec. 5, 2019, which claims priority, and the benefit of, U.S. Provisional Patent Application 62/775,733, filed on Dec. 5, 2018, each of which is hereby incorporated by reference in its entirety.

TECHNICAL FIELD

The present disclosure generally relates to a medical device, and more particularly, to a breathing apparatus with a breath detection software.

BACKGROUND

Some breathing apparatus can lack portability and require continuous monitoring of user condition and manual adjustment of breathing settings by health care personnel. In many cases, expensive breathing monitoring technologies such as CO2 capnography must be used in conjunction with a breathing apparatus, to determine effectiveness and make adjustments in settings during use. Some control methodologies and configurations are not readily adaptable for use with certain user conditions, for example, when the user is talking, during sleep, or when the user is connected to Continuous Positive Airway Pressure (CPAP) and/or Bilevel Positive Airway Pressure (BiPAP) machines, for example, during sleep apnea therapy.

SUMMARY

In an aspect of the present disclosure, the breathing apparatus includes a tubing configured to receive an input gas and a flow outlet airline in fluid communication with the tubing. The flow outlet airline is configured to supply an output gas to a user. The breathing apparatus further includes a breath detection airline configured to receive breathing gas from the user during exhalation by the user. The breathing apparatus further includes a pressure sensor in direct fluid communication with the breath detection airline. The pressure sensor is configured to measure breathing pressure from the user. The pressure sensor is configured to generate sensor pressure data indicative of breathing by the user. The breathing apparatus further includes a controller in electronic communication with the pressure sensor. The controller is programmed to detect breathing by the user based on the sensor breathing data received from the pressure sensor on a breath by breath basis.

The controller is programmed to command the breathing apparatus to supply the output gas to the user at predetermined times based on the predicted breathing by the user. The controller is programmed to filter the sensor breathing data to generate a filtered breathing data. The controller is programmed to generate a predictive curve graph based on the filtered breathing data, and the predictive curve graph is indicative of predictive breathing by the user over time. The controller is programmed to generate the predictive curve graph by calculating a moving average of past breaths by the user.

The controller is programmed to: compare the moving average with the filtered breathing data to determine whether the moving average is less than the filtered breathing data; and predict an inhalation of the user in response to determining that the moving average is less than the filtered breathing data. The controller is programmed to: compare the moving average with the filtered breathing data to determine whether the moving average is equal to or greater than the filtered breathing data; and predict an exhalation of the user in response to determining that the moving average is equal to or greater than the filtered breathing data.

The breathing apparatus can further include an exhalation conduit configured to receive exhalation gases from the user, a filter connected to the exhalation conduit, and an exhaust muffler in fluid communication with the exhalation conduit. The breathing apparatus includes an enclosure, and the pressure sensor and the controller are entirely disposed inside the enclosure. The exhaust muffler is disposed outside of the enclosure.

The present disclosure also describes a cloud-based breath detection software and patient monitoring system. The system includes a breathing apparatus including a controller, a patient monitor configured to monitor a vital sign of a user of the breathing apparatus, a pulse oximeter configured to measure and monitor an oxygen saturation or oxygen levels in the blood of the user of the ventilator, and a cloud-based software system in communication with the controller of the breathing apparatus, the pulse oximeter, and the patient monitor. The breathing apparatus includes a tubing configured to receive an input gas and a flow outlet airline in fluid communication with the tubing. The flow outlet airline is configured to supply an output gas to a user. The breathing apparatus further includes a breath detection airline configured to receive breathing gas from the user during exhalation by the user via the breath detection airline. The breathing apparatus further includes a pressure sensor in direct fluid communication with the breath detection airline. The pressure sensor is in communication with the controller of the breathing apparatus. The pressure sensor is configured to measure breathing pressure from the user, and the pressure sensor is in communication with the cloud-based software system through the controller of the breathing apparatus. The cloud-based software system is configured to determine a flow rate of the output gas supplied to the user by the breathing apparatus on a breath by breath basis based on data from the pressure sensor, the pulse oximeter, and the patient monitor. The cloud-based software system is configured to communicate the flow rate of the output gas to be supplied to the user to the controller. The controller is programmed to control the output gas supplied to the user based on the flow rate of the output gas determined by the cloud-based software system.

The cloud-based software system stores data from the pressure sensor, the pulse oximeter, and the patient monitor. The cloud-based software system is programmed to predict inhalation by the user based on measurements from the pressure sensor. The cloud-based software system is programmed to time stamp the measurements from the pressure sensor in order to predict the inhalation by the user. The cloud-based software system is programmed to generate a breath pattern of the user based on the measurements from the pressure sensor, and the breath pattern is used to predict the inhalation by the user. The cloud-based software system is programmed to determine effects of the flow rate of the output gas on physiological data of the user collected by the pulse oximeter and the patient monitor. The cloud-based software system is programmed to use a feed forward control to adjust the output gas to be supplied to the user by the breathing apparatus.

The present disclosure also describes a method for supplying an output gas to a user. In an aspect of the present disclosure, the method includes: monitoring a vital sign from the user using a patient monitor; monitoring an oxygen saturation or oxygen level in the blood of the user using a pulse oximeter; monitoring a breathing pressure of the user using a pressure sensor of a breathing apparatus; and controlling, by a controller of the breathing apparatus, the output gas supplied by the breathing apparatus based on the monitored vital sign, the monitored oxygen saturation or oxygen level in the blood of the user, and the monitored breathing pressure of the user.

The method can further include calculating a flow rate of the output gas based on the monitored vital sign, the monitored oxygen saturation or oxygen level in the blood of the user, and the monitored breathing pressure of the user. The method can further include determining effects of the flow rate of the output gas on physiological data of the user. The method can further include using a feed forward control to adjust the output gas to be supplied to the user. The method can further filtering data obtained from the pressure sensor.

The above features and advantages and other features and advantages of the present teachings are readily apparent from the following detailed description of the modes for carrying out the present teachings when taken in connection with the accompanying drawings.

BRIEF DESCRIPTION OF THE DRAWINGS

The accompanying drawings, which are incorporated into and constitute a part of this specification, illustrate implementations of the disclosure and together with the description, serve to explain the principles of the disclosure.

DETAILED DESCRIPTION

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Figure 1:
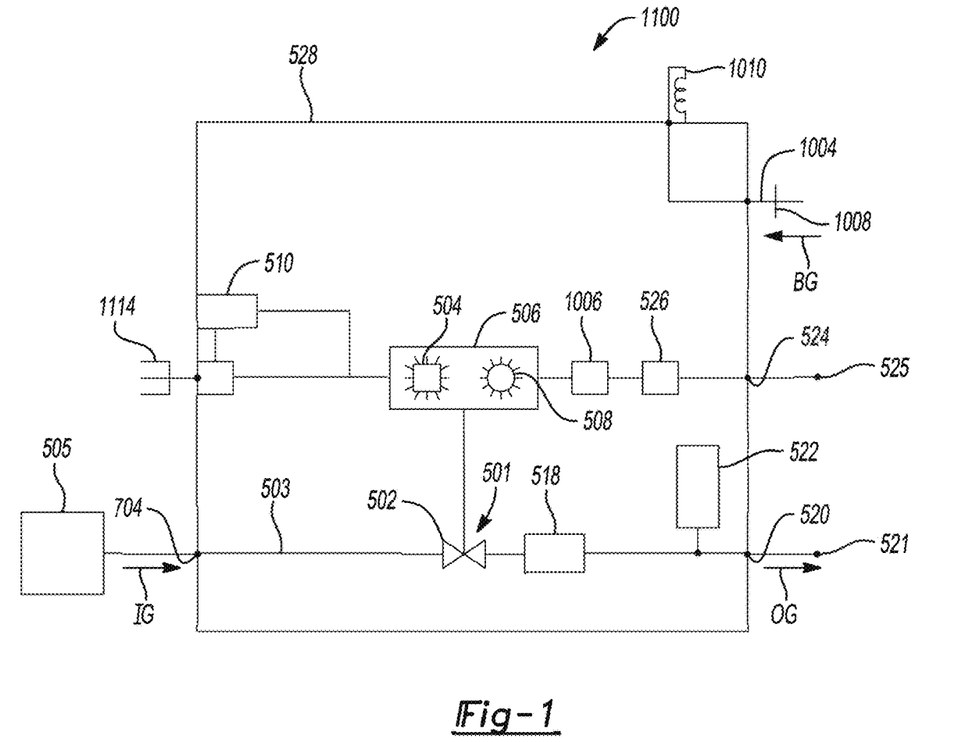
FIG. 1 is a schematic diagram of a breathing apparatus, such as a ventilator.

With reference to FIG. 1, a breathing apparatus 1100 includes valve 502, such as an on-off valve or an electronically controlled valve, configured to modulate a flow through a tubing 503. Accordingly, the valve 502 has at least an open state and a closed state. The valve 502 may be part of a valve arrangement 501. The valve arrangement 501 may therefore include one or more of the valves 502. It is also contemplated that the valve arrangement 501 may include other types of valves. Hence, the breathing apparatus 1100 can include valve 502 to minimize cost and weight. The breathing apparatus 1100 functions by receiving input gas IG from an input gas source 505 through the tubing 503. The tubing 503 is fluid communication with the input gas source 505 to allow the input gas source 505 to supply the input gas IG to the breathing apparatus 1100. As non-limiting examples, the input source 505 may be an air compressor, air blower, stationary oxygen concentrator, portable oxygen concentrator, air tank, and/or oxygen tank. A continuous flow of input gas IG enters the breathing apparatus 1100 through the tubing 503, and when the valve 502 opens, the flow rate of input gas IG and output gas OG is the same or at least substantially the same.

The ON-OFF cycles of the valve 502 are controlled using a controller 504, such as a microprocessor or microcontroller unit. The controller 504 may be part of an electronic board 506, which can contain additional electronic components including but not limited to: power electronics, resistors, capacitors, alarms 508, and copper traces. The electronic board 506 may include one or more alarms 508. The alarms 508 can, for example, be used to warn the user of one or more of the following conditions: tubing disconnections, electrical or air supply failure, high peak airway pressure, auto-positive end-expiratory pressure (auto-PEEP), high gas supply pressures, and/or no spontaneous breathing. Further, this electronic board 506 may be utilized as a battery management system for a portable ventilator device that is battery powered.

The breathing apparatus 1100 can include an electrical power source 510, such as a portable rechargeable Li-Ion battery pack or another suitable portable battery assembly. As a non-limiting example, Nickel Metal Hydride (NiMH) Rechargeable Batteries and an 8-battery holder may comprise the electrical power source 510. This is electrically designed to be a 12V circuit as a battery backup in case of main power supply failure, which makes the power electronics on the electronics board 506 simpler. The electrical power source 510 may be recharged after use by AC power module operation when the main power supply is back online. Each AAA cell is 1.2V with a rated capacity of 800 mAH. These alkaline batteries are safe and effective. A power receptacle 1114 is electrically connected to the electrical power source 510 and can function as a recharging interface, such as a port or cable, thereby allowing the electrical power source 510 to be recharged. As non-limiting examples, the power receptacle 1114 may be a Universal Serial Bus-C (USB-C), a USB, a micro-USB, or other charging interfaces. The electrical power source 510 may be electrically connected to the electric board 506 to supply electricity to the controller 504 and the alarms 508.

This controller 504 can be in the form of an FPGA, MCU, single board computer, ASIC, PLC on a chip, and/or other processing or computer hardware that can control the ON/OFF or OPEN/CLOSE cycles of a solenoid valve 502. The valve 502 can be controlled using fluidic chips or other non-conventional or pneumatic methods of valve control, such as air cylinder actuations. For example, an air cylinder or pressure actuator and a check valve can replace the valve 502.

The pressured output gas OG may be outputted in a plurality of different waveforms, such as descending ramp, ascending ramp, sinusoidal, and/or square wave form, among others. Further, these output gas waveforms and flow rates may be adjusted based on breathing airway pressure and/or flow measurements from a second lumen air line. In the presently disclosed breathing apparatus 1100, the flow control and breathing measurements are separately obtained via dual lumen airlines. This dual lumen airline setup prevents electrical signal interference and saturation of the gas output pressure/flow and the breathing measurement pressure/flow sensor sensors found in prior art oxygen conserving devices and ventilators. Further, this also allows for the use of much more sensitive pressure sensors for detecting breathing. In other mechanical ventilators, single lumen tubes are used and, as such, the flow output and breath "triggering" or detection are done in the same airline. Further, in other breathing apparatus, only inhalation is detected. In other breathing apparatus, exhalation and inhalation breathing flows are spearhead using one-way check valves which comprise the dual limb ventilator circuit. In the mechanical breathing apparatus 1100 of the present disclosure, the proximal pressure line is bidirectional (i.e., there are no check valves) and, as such, there is no pressure or flow "triggers" but rather patterns in breathing are mathematically computed based on nasopharynx pressure and/or breath detection sensor waveforms. In experimental use, by positioning the pressure sensors for breath detection in a separate lumen from the lumen used for gas output, it was found six times (6×) more sensitive pressure sensors can be utilized with a dual lumen setup for detecting breathing compared to single lumen pressure sensors. The breathing apparatus 1100 may also have rest, exercise, and/or sleep settings.

The flow rate of this continuous output gas OG to the patient is measured using a flow sensor 518. This flow sensor 518 is in fluid communication with the tubing and can include a plurality of sensor methodologies. For example, the flow sensor 518 may utilize the thermo-transfer principle, also known as the calorimetric principle, to measure large ranges of gas flow rates when the gain factor of the flow sensor 518 is specifically calibrated and tested, such that the sensor output is amplified and two point trimmed at zero flow as well as a secondary flow rate point to optimize linearity within a certain flow rate range, such as 0-40 standard liter per minute (SLPM) gas flow. Under this thermo-transfer principle, inside the flow sensor module 518, a temperature sensor (not shown) is heated periodically by a heater element (not shown). The flowing gas absorbs heat energy and conducts it away. The resulting temperature change is an indication of flow, which translates to an analog voltage value that is then correlated to a flow output curve based on experimental data from the original equipment manufacturer (OEM) or sensor manufacturer during calibration and/or testing. Generally, this flow sensor 518 is a flow-through type sensor, wherein the flow sensor 518 includes a barb fitting inlet that connects to the tubing 503, as well as a barb outlet to the flow outlet airline 520 with minimal resistance of fluidic loss. This flow outlet airline 520 can connect to a 22 mm breathing tube, hose barb, adapter, or other tubing connection thereafter. Further, this flow outlet airline 520 can also be fluidly coupled to an air entrainment device 522. In the present disclosure, the term "air entertainment device" means a physical object configured to entrain a fluid, such as a nozzle, a Venturi conduit, a conduit using the Coanda effect, a conduit using the Jet principle, or another conduit capable of entraining a fluid. The air entrainment device 522 is in direct fluid communication with the tubing 503. The flow sensor 518 is upstream of the air entrainment device 522, and downstream of the valve 502 to allow the flow sensor 518 to provide the controller 504 with reliability sensing data without interference from the air entrainment device 522. Therefore, the controller 504 is in electronic communication with the flow sensor 518 and is programmed to receive data from the flow sensor 518. The controller 504 is in electronic communication with the valve 502 and is programmed to control the valve 502 based on the data received from the flow sensor 518. The flow sensor 518 can alternatively be other types of sensors, such as: turbine-type flow meters, rotometers, and membrane based differential pressure and temperature sensors that can be used to calculate flow rates, which can work especially well for laminar type or large volume/low pressure flows. the flow outlet airline 520 includes an airline outlet 521.

The breathing apparatus 1100 can also include an alarm 508 in the electronic board 506. The alarm 508 can be an auditable alarm designed for medical applications and can be recognized under the International Electrotechnical Commission (IEC) 60601-1-8 standard. This alarm 508 is a component of the electronics board 506 that can include a specially designed speaker-housing assembly with no circuitry. Other alarm types can also be utilized including but not limited to: piezoelectric type speakers, audio amplifiers, and/or electromagnetic speakers. With this alarm 508, the original equipment manufacturer (OEM) only needs to input a simple square wave signal with one frequency component, and the other needed harmonic sound frequencies are generated acoustically. This greatly simplifies implementation of an audible alarm sound in an IEC 60601-1-8 standard since the harmonic peaks are designed to be acoustically equal to the sound level required under IEC 60601-1-8. This alarm 508 relies on the 2nd option for compliance, a melody table listed in Annex F of the IEC 60601-1-8 standard where specific medical conditions/applications are assigned individual melodies. These melodies are essentially little tunes that change in pitch per the tables in Annex F. The objective is that the medical personnel using medical equipment with alarms that use these melodies will become familiar with them which can help the medical personnel respond more quickly and more appropriately when a specific melody alarm sounds. This breathing apparatus 1100 utilizes the alarm 508 to generate high, medium, or low priority warning sounds depending on the condition of the patient or malfunctions with ventilator equipment such as tubing disconnects. The audible sound has a fundamental frequency <1000 Hz, with at least 4 harmonic frequencies within 15 dB of the fundamental frequency. This alarm 508 has specific waveform and timing requirements for the three priority sounds, which includes a sound rise time specified by the alarm manufacturer. Alarm settings can include, but are not limited to, the following: if $O_2$ input from inlet 704 flows, but no breathing/exhalation is detected within 6 seconds, sound alarm—low priority; if the electrical power source 510 is being used—medium priority; if $O_2$ connected in wrong conduit (e.g., breath detection airline 524, flow outlet airline 520, or an $CO2$ exhalation conduit 1004), sound alarm—high priority; if the pressure measured during inspiration using peak airway sensor 1006 is less than 40 cmH2O for more than 3 breaths in a row, sound alarm—high priority; if the CO2 exhalation conduit 1004 gets disconnected from ventilator 1000 within 6 seconds of assist or control breath output, sound alarm—medium priority; if the flow outlet airline 520 gets disconnected from ventilator 1000 within 6 seconds of assist or control breath, sound alarm—high priority.

During operation, user spontaneous breathing is detected using a separated breath detection airline 524 and an ultra-sensitive pressure sensor 526 for measuring breathing pressures (e.g., nasopharynx pressure). The breath detection airline 524 includes an airline inlet 525. The airline inlet 525 is separated from the airline outlet 521 of the flow outline airline 520 to minimize interference and therefore increase the accuracy of the pressure sensor 526. The pressure sensor 526 is in fluid communication with the breath detection airline 524. This breath detection airline 524 is configured to be connected to a 22 mm breathing tube, hose barb, adapter, or other tubing connections. The breath detection airline 524 is not in fluid communication with the flow outlet airline 520. By fluidly separating the breath detection airline 524 from the flow outlet airline 520, breathing pressures (e.g., nasopharynx pressures) can be measured without signal interference from the pressure/flow output from the breathing apparatus 1100, which would otherwise saturate the ultra-sensitive pressure sensor 526 required to measure the breathing pressures (e.g., nasopharynx pressures) from the user of the breathing apparatus 1100. In other ventilators and oxygen concentrators, a single airline is generally utilized in which a flow or pressure trigger threshold, ex. −0.13 cm $H_2O$ pressure, is used to determine the start of inhalation. This generally creates substantial lag in the ventilator gas output or false breathing triggers. Further, this necessitates the use of far less sensitive pressure sensors to prevent the pressure sensor from getting saturated from the output flow gas from the ventilator. Also, if flow is triggered based on a flow ramp, there can still exist substantial signal interference using a single airline.

In the presently disclosed breathing apparatus 1100, a breath detection software is used to predict transitions in breathing states and breathing time states, for example: transition from inhale to exhale, 70% inhalation time, transition from exhale to inhale, predicted PEEP based on % of exhalation. This breath detection software functions by measuring breathing pressures (e.g., nasopharynx pressures) using a separated breath detection airline 524, then storing the voltage values from the pressure sensor 526 in the controller 504 (e.g., microcontroller) RAM or EEPROM. For this reason, the controller 504 is in electronic communication with the pressure sensor 526. Breath transition states and timing predictions are detected through one or more mathematical calculations involving the pressure sensor voltage data including but not limited to: data filtering, differentiation, integration, linear regression analysis and linearizations, moving average calculations, Taylor series approximations, steady state error compensation, model predictive control, proportional control, fuzzy control theory, ODEs, radial basis functions, quadratic-program approximation, feedforward control, adaptive control, PI and/or PID control, SISO control schema, and Laplace transformations. A moving average calculation can be used such that, if the filtered pressure sensor data falls below the moving average, a transition from an inhale to an exhale is predicted.

Other sensors can also be used independently, in combination with, or to replace the pressure sensor(s) 526 described herein to measure data trends in breathing, implement predictive breath detection software algorithms, and/or actuate at certain threshold values and/or ramps including but not limited to: flow sensors, CO2 gas concentration sensors, O2 gas concentration sensors, temperature sensors, humidity sensors, volume sensors, and/or acoustic sensors. This breath detection is used to determine when to output the output gas OG, which can include compressed air, oxygen, or a mixture thereof, to the patient at the correct time in order to provide pressure/ventilatory support, as well as facilitate effective lung gas exchange, ventilation, and manage arterial blood gases (ABGs) such as $PaCO_2$ and $PaO_2$. Accordingly, the pressure sensor 526 is configured to generate sensor data indicative of breathing by the user, and the controller 504 is programmed to detect the breathing of the user based on the sensor data received from the pressure sensor 526.

The components and electromechanical subassemblies of the breathing apparatus 1100 are contained within an electronics enclosure 528, which can be manufactured using a plurality of manufacturing methods including but not limited to: injection molding, 3D printing, CNC machining, sheet metal fabrication, PCBA, wire harnessing, and other manual or automated manufacturing techniques not described herein.

With continued reference to FIG. 1, the breathing apparatus 1100 includes an electrical power source 510 (e.g., battery) inside the enclosure 528. The electrical power source 510 is electrically connected to the controller 504. The breathing apparatus 1100 further includes a power receptacle 1114 electrically connected to the electric power source 510, the controller 504, and the electric board 506. The breathing apparatus 1100 does not include $CO_2$ exhalation valve. For invasive ventilation, a single limb circuit would be required. This type of configuration would be more suited for breathing apparatus with a focus on non-invasive home ventilation, where the capability of optional but less frequent use invasive ventilation is desired. This configuration without the active $CO_2$ exhalation valve inside the breathing apparatus 1100 substantially reduces power consumption and weight compared to the other breathing apparatus, allowing for lightweight portability with battery power. The breathing apparatus 1100 includes an $CO_2$ exhalation conduit 1004 configured to receive exhalation gas BG from the user. The inlet 704, the flow outlet airline 520, the breath detection airline 524, and the $CO_2$ exhalation conduit 1004 can include tubing connectors. For example, the inlet 704, the flow outlet airline 520, the breath detection airline 524, and the $CO_2$ exhalation conduit 1004 can include quick change connectors such that modifications to the patient circuit and/or gas source can be made, allowing components to be replaced. The $CO_2$ exhalation conduit 1004 is configured to receive exhalation gases from the user. The breathing apparatus 1100 includes the air entrainment device 522, which in some configurations is a fixed $FiO_2$ based on mechanical design and hence should be easy to remove and replace in order for a user to adjust $FiO_2$. The breathing apparatus 1100 includes a bacteria/viral filter 1008 attached to the $CO_2$ exhalation conduit 1004. Patient expired gas flows back through bacteria/viral filter 1008, which includes a 22 mm breathing tube connector to minimize exhalation resistance, before coming into contact with any internal device components. This viral/bacterial filter 1008 can include a standard coaxial International Standards Organization (ISO) connectors (e.g., ISO 5356-1 standard) that connect to standard breathing tubes using 15 mm internal diameter (ID)/22 mm outer diameter (OD) connectors for applications in breathing circuits, scavenging circuits, mechanical ventilation, and manual ventilation, including bag valve mask (BVM). This viral/bacterial filter 1008 is designed for single-patient use and, in some embodiments, can have bidirectional airline, be in-line, low flow resistance of 1.5 cm $H_2O$ pressure at 60 LPM, hydrophobic and electrostatic filtering properties, dead space of 45 mL, and ultrasonically welded. An heat and moisture exchange (HME) filter or active heated humidification system and/or airline can be added to the flow outlet airline 520 to heat and moisturize the output gas OG output to the patient in order to prevent drying of airways and promote patient health/comfort. Patient gas is expelled to the atmosphere after flowing through bacteria/viral filter 1008 and through an exhaust muffler 1010. The exhaust muffler 1010 is in communication with the $CO_2$ exhalation conduit 1004 and is disposed outside the enclosure 528 to safely expel the $CO_2$ gases.

The breathing apparatus 1100 can include a peak airway pressure sensor 1006 in direct fluid communication with the pressure sensor 526. An LCD screen can indicate, using a graphic or light emitting diode (LED) bar, when adjustments to gas source input flow should be made based on the peak airway pressure sensor measurements measured by the peak airway pressure sensor 1006. Generally, gas source flow input should be increased when $SpO_2$ saturation is less than 90%, which can be measured using a separate patient/vital signs monitor and/or pulse oximeter and decreased when peak airway pressure is high (i.e., more than 35 cm $H_2O$). A fixed tidal volume delivered per breath can be provided to user via the LCD screen or via a separate instruction manual based on adjustment of wall $O_2$ supply flow rates. The user can increase tidal volumes delivered to patient by increasing $O_2$ flow rate input at the inlet 704. The inlet 704 can be an input gas source connector and can include a barb fitting, diameter-index safety system (DISS) connectors, quick connectors, and others. For example, the input gas source connector can be a ¼" National Pipe Tapered (NPT) barb fitting that connects to 50 psi hospital wall pipeline $O_2$ supply or $O_2$ tank using ¼" internal diameter (ID) oxygen tubing. The inlet 704, the flow outlet airline 520, the breath detection airline 524, and a $CO_2$ exhalation conduit 1004 can include tubing connectors. For example, the inlet 704, flow outlet airline 520, breath detection airline 524, and the $CO_2$ exhalation conduit 1004 can include quick change connectors such that modifications to the patient circuit and/or gas source can be made, allowing components to be replaced. The $CO_2$ exhalation conduit 1004 is in direct fluid communication with the viral/bacterial filter 1008 and exhaust muffler 1010 to facilitate filtering and exhausting the exhalation gases outside the enclosure 528. Further, the $CO_2$ exhalation conduit 1004 is configured to receive exhalation gases from the user of the breathing apparatus 1100. The breathing apparatus 1100 includes the air entrainment device 522, which in some configurations is a fixed $FiO_2$ based on mechanical design and hence should be easy to remove and replace in order for a user to adjust $FiO_2$.

Figure 2:
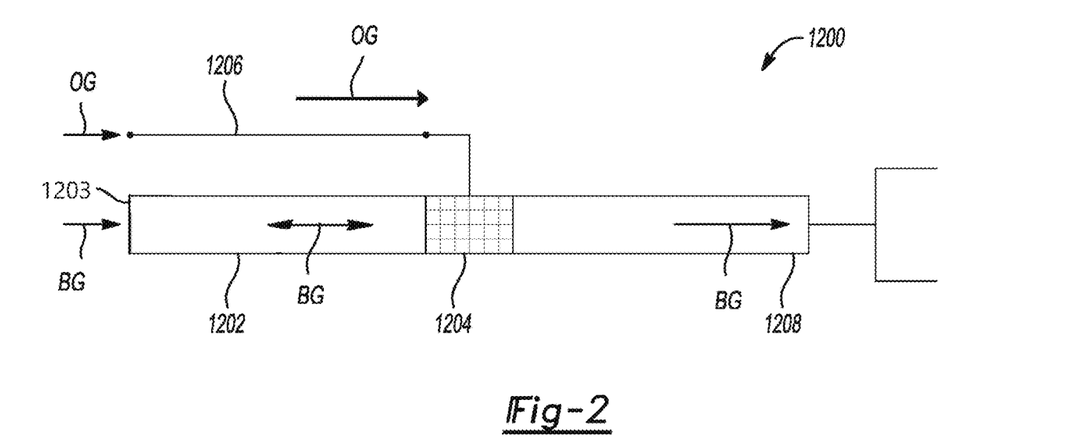
FIG. 2 is a schematic diagram of an invasive circuit using a breathing tube, an adapter, and an oxygen tubing.

With reference to FIG. 2, a non-invasive circuit 1200 can be connected to the breathing apparatus 1100 or other breathing apparatus described herein. The non-invasive circuit includes a breathing tubing 1202 (e.g., 22 mm tubing), an adapter 1204, an oxygen tubing 1206, and a patient interface 1208. This breathing tubing 1202 and any other tubing described herein can have various connector and inner tubing diameter sizes not specified in this disclosure. An inlet 1203 of the breathing tubing 1202 connects to the breath detection airline 524 to minimize flow resistance and measure breathing pressures (e.g., nasopharynx pressures) accurately without signal interference from the oxygen flow. The oxygen tubing 1206 can be connected at the outlet 521 of the airline flow outlet airline 520. The tidal volume from the breathing apparatus 1100 can be output to the patient in a unidirectional flow from the inlet 1203 of the oxygen tubing 1206 to the barb inlet of the adapter 1204, and then to the patient interface 1208 either during a control or assist breath. The adapter 1204 serves as a connection point for the oxygen tubing 1206 and the breathing tubing 1202, allowing tidal volume flow output to the patient interface 1208 as well as bidirectional breath detection software data measurements using the 22 mm breathing tubing 1202 as a flow conduit to the sensors inside the breathing apparatus 1100, such as the pressure sensor 526 with a pressure measurement range of 0.018 PSIG. The non-invasive circuit 1200 is configured to be disposed outside the enclosure 528.

Figure 3:
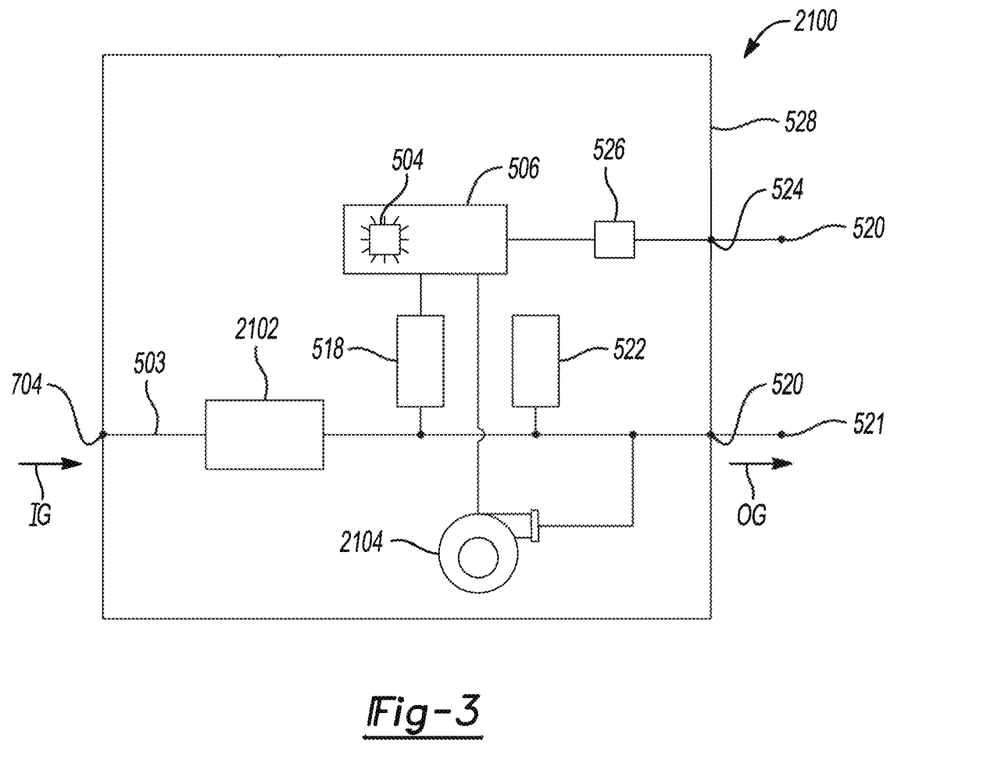
FIG. 3 is a schematic diagram of a breathing apparatus that can function as BiPAP, CPAP device, an $O_2$ concentration, and/or ventilator with different modes.

FIG. 3 illustrates a breathing apparatus 2100 that that can function as bilevel positive airway pressure (BiPAP) device or continuous positive airway pressure (CPAP) device, oxygen ($O_2$) concentrator, and/or breathing apparatus 2100 with different modes. The breathing apparatus 2100 includes an enclosure 528, a tubing 503 configured to receive the input gas IG, and an internal oxygen concentrator 2102 in fluid communication with the tubing 503. The tubing 503 is entirely or at least partially disposed inside the enclosure 528 to minimize the space occupied by the breathing apparatus 2100. The internal oxygen concentrator 2102 is integrated with the breathing apparatus 2100 and is therefore entirely disposed inside the enclosure 528 to minimize the space occupied by the breathing apparatus 2100. The internal oxygen concentrator 2102 can be used to generate enriched oxygen flow to the patient (i.e., output gas OG). The internal oxygen concentrator 2102 can be turned ON or OFF either automatically using electronic control from the controller 504 (e.g., a microcontroller unit) or via user adjustment of a human-computer interface, including, but not limited to, knobs, touchscreens, and/or switches. The internal oxygen concentrator 2102 can produce and/or deliver oxygen on demand based on a patient's breathing needs, provide a continuous flow of oxygen, and/or produce an oscillatory or irregular oxygen output pattern to the user via the flow outlet airline 520.

The breathing apparatus 2100 can include an air entrainment device 522 in fluid communication with the internal oxygen concentrator 2102. The air entrainment device 522 is downstream of the internal oxygen concentrator 2102 to entrain the flow of oxygen originating from the internal oxygen concentrator 2102. The enriched oxygen exiting from the oxygen concentrator 2102 can be used to entrain room air using the air entrainment device 522. The breathing apparatus 2100 can additionally include an air blower 2104 in fluid communication with the internal oxygen concentrator 2102 and the tubing 503. The air blower 2104 may be in communication with the controller 504. The controller 504 can be programmed to adjust the output gas OG to the patient by the air blower 2104. The air entrainment device 522 could be substituted for or used in combination with the air entrainment device 522 to perform air-$O_2$ mixing. In some embodiments, oxygen could be delivered to the patient during useful phases of respiration as measured using the breath detection airline 524 and the pressure sensor 526. After oxygen is delivered during the useful phase of respiration, a positive-end expiratory pressure (PEEP) can be provided using the air blower 2104 to prevent lung collapse in patients with chronic lung diseases, especially those who are mechanically ventilated. This output pressure from the air blower 2104 may be controlled using the controller 504 or via user input from a human-computer interface 2406 (FIG. 7), at specific ranges for example 0.1-20 cmH$_2$O pressure. The output flow (e.g., output gas OG) may also be controlled using the controller 504. For example, the controller 504 may control the output gas OG by controlling the blower motor speed of the air blower 2104, voltage, and/or power consumption of the breathing apparatus 2100. In some embodiments, an additional pressure sensor can be added to the outlet airline 520 to measure the output pressure of the output gas OG to the patient.

In some embodiments, the pressure of the output gas OG provided to the patient may be controlled by the controller 504 or the user. The air blower 2104 may control the output airflow (e.g., output gas) to modulate the pressure based on a setpoint. For example, if the output pressure of the O$_2$ and/or compressed air tidal volume from the outlet airline 520 is 6.8 cmH$_2$O at a flow of 40 LPM and the setpoint is 3.9 cmH$_2$O, the air blower 2104 can output 1 cmH$_2$O pressure at 40 LPM flow to achieve the setpoint. In some embodiments of the invention, oxygen pulses could be output intermittently at a frequency greater than an inhalation frequency. In some embodiments, during a period of useful respiration one or more pulse(s) of oxygen could be output followed in terms of timing by one or more pulse(s) of air from the air blower 2104. The lengths of these oxygen and/or blower air pulses can be different or the same as each other.

In another embodiment, the air blower 2104 may be used as an integrated or separate BiPAP/CPAP machine, wherein modes and settings could be selectable, deactivated, and/or activated by the user, healthcare provider, and/or DME based on payment/billing code. For example, the DME supplier may remotely, using software only, enable the breathing apparatus 2100 for use as a non-invasive ventilator if the patient were only prescribed a non-invasive ventilator. If a patient, however, requires supplemental oxygen one year later, the DME can remotely enable this feature using software and then subsequently bill Medicare or an insurance provider for that add-on. In some embodiments, this can also include integrated oxygen and CPAP for obstructive sleep apnea patients with overlap syndrome.

In some embodiments, the blower pressure of the air blower 2104, including IPAP and PEEP, can be controlled, via the controller 504, by the user, clinician, and/or healthcare provider, with the settings recommended or based on the patient prescription and/or real time physiological characteristics such as breathing, pulse oximetry data, vital signs data, etc. For BiPAP, this generally means that the pressures of the air output can range between 5-20 cmH$_2$O IPAP, and at least 3 cmH$_2$O less for PEEP, for example 2-17 cmH2O PEEP. These IPAP and PEEP variables can be independently or jointly controlled, by the machine software itself, clinician, and/or user. For CPAP or IPAP, the pressure for IPAP and PEEP would be the same. Hence, only one pressure setpoint would be set. In one embodiment, tidal volume and flow rates of the air blower 2104 could also be controlled by the controller 504 (e.g., microprocessor) of the breathing apparatus 2100, a clinician, and/or the user to maximize user comfort, with guidelines based on the patient interface used which could vary from user to user based on patient physiology and mask leakage. This PEEP could also be determined based on peak airway pressure or predicted using the breath detection software. In some embodiments, the breathing apparatus 2100 can also include wireless communication technology and/or features that allow the breathing apparatus 2100 to function as an at-home sleep test, and/or at-home oxygen test, and provide patient monitoring for the clinician.

Figure 4:
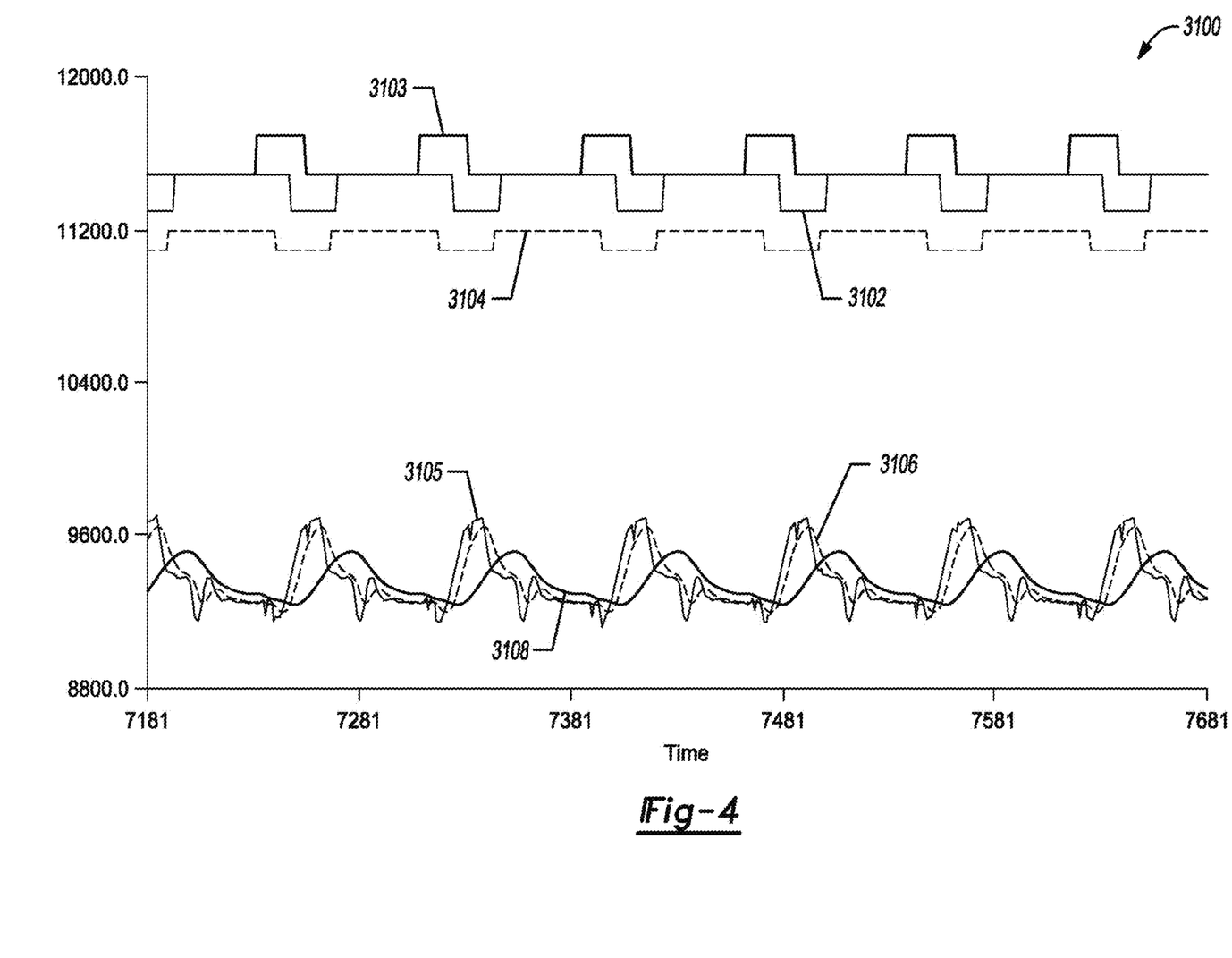
FIG. 4 is a breath detection predictive curve software graph.

FIG. 4 illustrates a breath detection predictive curve software graphs 3100. In FIG. 4, the horizontal axis represents time. Further, in FIG. 4, the first breath detection graph 3102 at the top represents software that predicted breath using measurements from the pressure sensor 526. As discussed above, the pressure sensor 526 can measure breathing pressures (e.g., nasopharynx pressure) from the user of a breathing apparatus, such as breathing apparatus 1100. However, it is envisioned that the breath detection predictive software graphs 3100 along with the method (or algorithm) 2500 can be executed in breathing apparatus 1100 or other breathing apparatus described herein. As discussed above, the breathing apparatus 1100 (or other breathing apparatus described herein) can be, but not limited to, Continuous Positive Airway Pressure (CPAP) machine or Bilevel Positive Airway Pressure (BiPAP) machines. Thus, the presently disclosed predictive breath detection software can be used with any breathing apparatus capable of supplying output gas OG to a user. The second detection graph 3104 at the top represents lung simulator breath detection using an IngMar Medical ASL5000™ lung simulator. The graph 3103 at the top represents the flow output to the user during testing determined based on the first detection graph 3102, the second detection graph 3104, or both. The controller 504 is programmed with a control algorithm for predicting breathing and outputting flow at certain specified times. This control algorithm may include a lag compensation algorithm. This lag algorithm can allow for the correction of systemic inaccuracies in predictive breath detection, such as overshoot, and allow for flow output to be output, for example, earlier than predicted by the breath detection software. Thus, the controller 504 is programmed to generate a flow output graph (e.g., graph 3103) as a function of time based on the first detection graph 3102 and/or the second breath detection graph 3104 and command the breath apparatus 1100 (or any other breathing apparatus described herein) to supply output gas OG to the user in accordance with the flow output graph 3103. The actual pressure data graph 3105 at the bottom represents actual sensor data (obtained from the pressure sensor 526) in terms of voltage readings. The actual sensor data obtained from the pressure sensor 526 can be filtered (with for example a low pass filter) and is represented by the filtered pressure sensor data graph 3106. Using the filtered pressure sensor data, a predictive curve graph 3108 can be generated. In some embodiments, the controller 504 can calculate a moving average based on past breaths detected. If the moving average is less than the filtered pressure sensor data 3106, then an inhalation is predicted. If the moving average is equal to or greater than the filtered pressure sensor data 3106, then an exhalation is predicted. The controller 504 can then command the breathing apparatus, such as, but not limited to, the mechanical breathing apparatus 1100, to supply the output gas OG to the user on a breath by breath basis based on the predicted exhalation and inhalation pattern of the user.

Figure 5:
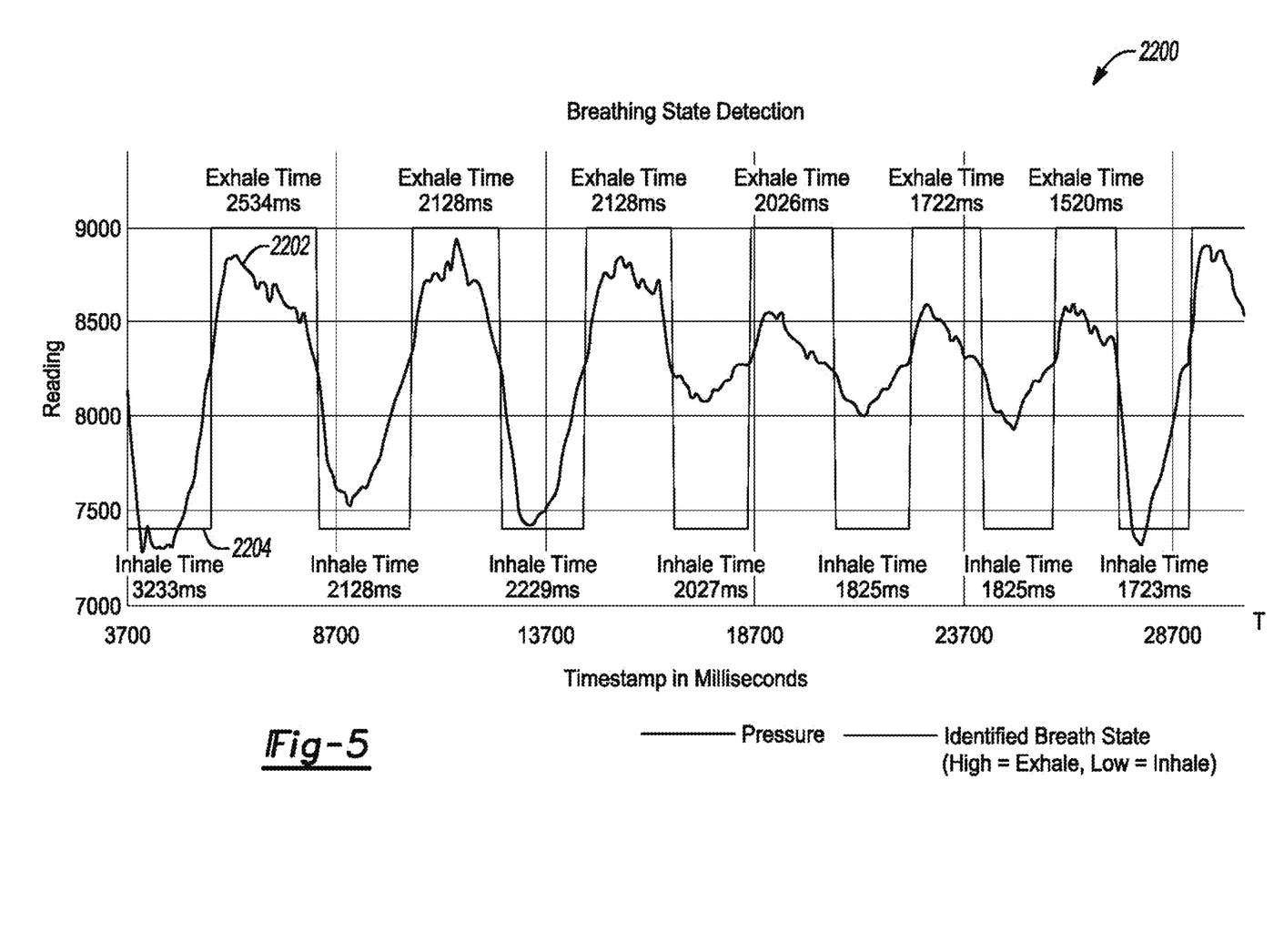
FIG. 5 is a graph of pressure reading v. time used to identify the breathing state of a user of a breathing apparatus.
Figure 6:
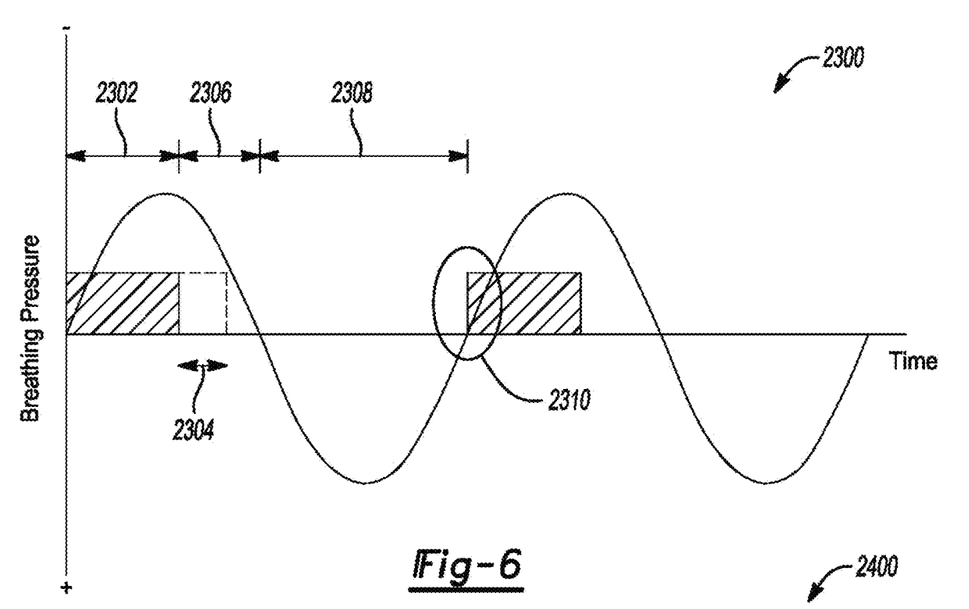
FIG. 6 is a tidal volume graph compared with a breathing cycle and a breathing apparatus operation.

FIG. 5 illustrates that breathing timing can be predicted using measurements from the pressure sensor 526 as shown in the graph 2200. The graph 2200 plots the measurements or readings 2202 of the pressure sensor 526 versus time T. For example, during the first breath 2202, an inhalation time of 3233 milliseconds is predicted and an exhalation time of 2534 milliseconds is predicted. The readings 2202 of the pressure sensor 526 at each time T may be saved to the controller 504 and/or may be uploaded to a cloud-based software 2408 (FIG. 6). In the graph 2200, the horizontal axis represents time stamps. The readings 2202 can be used by a control algorithm for pattern analysis or treatment. As shown by the plot 2204, the control algorithm may determine that inhalation occurs when the reading 2202 is equal to or less than a predetermined minimum threshold, and exhalation occurs when the reading 2202 is equal to or greater than a predetermined maximum threshold. The readings 2202 are time stamped and, the controller 504 and/or the cloud-based software 2408 may determine an inhalation and exhalation pattern based on the time stamped reading 2202. As a non-limiting example, the readings 2202 may be time stamped continuously or every 5000 milliseconds to generate a breath pattern that will be used to predict the inhalation of the user. However, it is envisioned that the readings 2202 may be time stamped at different time intervals. Additionally, or alternatively, the readings 2202 may be time stamped at specific transition points. For example, the readings 2202 may be time stamped when the reading 2202 is equal to or less than the predetermined minimum threshold (and inhalation is detected), and when the readings 2202 are equal to or greater than the predetermined maximum thresholds (when exhalation is detected). However, it is contemplated that the readings 2202 can be time stamped in real time (i.e., continuously) to detect the inhalation and exhalation by the user as well as the duration of the inhalation and exhalation. The readings 2202 may be used for traceability or correlation with other body measurements. In a non-cloud configuration, the control algorithm and the data collected are not stored on the cloud-based software system 2408 but rather on the controller 504 of the breathing apparatus 2404 and/or the controllers of the patient or vital sign monitor 2402 and/or the pulse oximeter 2406, or in a database in communication with one or more of these, and/or any other suitable breathing apparatus. In other words, the data and control algorithm can be localized into the controller (e.g., controller 504) or a local server of a breathing apparatus 1100.

Figure 7:
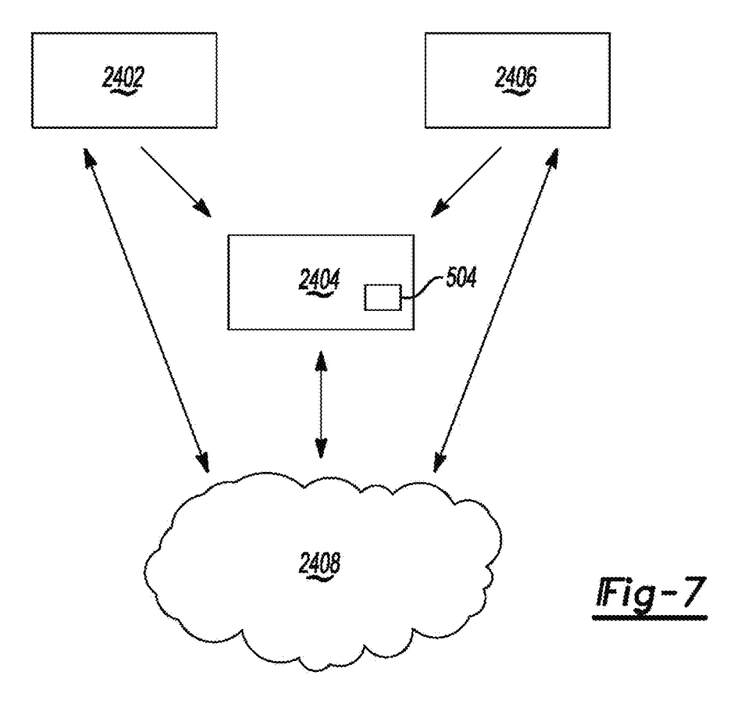
FIG. 7 is a schematic diagram of a breathing apparatus with cloud-based breath detection software and patient monitoring.

FIG. 6 illustrates a tidal volume graph 2300 compared with breathing cycle and ventilator device operations. This tidal volume graph 2300 is meant to represent that of a breathing apparatus 1100 (or another breathing apparatus described herein). As illustrated in FIG. 6, a tidal volume is output during a period of the user's respiration (time period 2302 while the valve 502 is open). In spontaneous breathing patients, this period of respiration is generally near the end of exhalation (for example the 90% exhalation time to approximately the 70% time of inhalation), because the last 30% of the inhalation (time period 2302) is anatomical deadspace where no useful gas exchange in the lungs occurs. Further, this tidal volume output can be a fixed and/or variable volume (for example between 50-2000 mL of gas) and can be adjusted by the user manually or may be adjusted automatically by the breathing apparatus, such as, but not limited to, the breathing apparatus 1100. In some embodiments, the variable volume output can be adjusted on a breath by breath basis by the controller 504 based on user physiological data such as heart rate, blood pressure, $PaO_2$, $PaCO_2$, and/or breathing gas concentrations from the user which can include oxygen %, nitrogen %, $CO_2$%, and/or trace gas concentrations. Some of this physiological data can be collected using a patient monitor and/or pulse oximetry system 2402, 2406 (FIG. 7). This physiological data can be stored on the controller 504 and/or the cloud-based software 2408. The physiological data may be correlated with the breathing timing data collected to optimize, for example, the flow rate of the output gas OG supplied to the user of the breathing apparatus 1100 (or another breathing apparatus described herein). In some embodiments, the patient monitor and/or pulse oximetry system may interface with the breathing apparatus 1100 (or another breathing apparatus described herein) via wired or wireless communication. This tidal volume may be a fixed and/or variable time duration. In some embodiments, the variable time duration of tidal volume output may be during spontaneous breathing (assist breath). Alternatively, the tidal volume output may be fixed tidal volume output during non-spontaneous breathing (control breath). The duration of tidal volume output may be time controlled, pressure controlled, flow controlled, volume controlled, and/or a combination of these control methodologies. When this tidal volume is being output to the patient during the time period 2302, the valve 502 opens. After the tidal volume is output to the patient, the valve 502 closes during a time period 2306, such that an inspiratory hold time is created. This inspiratory hold time is generally 30% of tidal volume output duration timing (time period 2304) and is meant to facilitate gas exchange in the lungs, as well as measure plateau and peak airway pressures to evaluate the breathing apparatus pressure support provided to the patient. This monitoring of plateau and peak airway pressures can allow the user to adjust tidal volumes and/or inspiratory flows to minimize the risk of barotrauma or associated lung injuries (VALI). After the inspiratory hold time is complete, the $CO_2$ exhalation conduit 1004 opens for the duration of exhalation (i.e., time period 2308) until a new tidal volume is output by the breathing apparatus 1100 (or another breathing apparatus described herein). In one embodiment, PEEP can be predicted based on the exhalation time of the tidal volume output, which is based on the measurement or estimation of expiratory pressures as well as pressure of tidal volume gas. This tidal volume output start time for predictive breath detection, for example 98% exhalation time as shown in area 2310, can be adjusted breath by breath by the ventilator 1000 such that breathing synchrony for the patient improves over time during use.

With reference to FIG. 7, a cloud-based breath detection software and patient monitoring system 2400 is illustrated. By way of example, a "cloud-based" system, as that term is used herein, can refer to a system which includes software and/or data which is stored, managed, and/or processed on a network of remote servers hosted in the "cloud", e.g., via the Internet, rather than on local severs or personal computers. The system 2400 includes a patient or vital sign monitor 2402, a breathing apparatus 2404 (e.g., a ventilator, CPAP, a BiPAP or another device subtle to provide output gas OG to a user) in communication with the patient or vital sign monitor 2402, and a pulse oximeter 2406 in communication with the breathing apparatus 2404. The pulse oximeter 2406 is configured to monitor and communicate oxygen saturation or oxygen levels in the blood of a patient. The patient or vital sign monitor 2402 is configured to monitor and communicate patient data, such as vital signs including but not limited to blood pressure, $SpO_2$, and heart rate to the breathing apparatus 2404 (e.g., breathing apparatus 1100). The breathing apparatus 2404 is in communication with cloud-based software 2408 and has internal electronics that allow for input data connections such as a serial bus, Internet of Things (IoT), and/or wireless communications capabilities. The breathing apparatus 2404 can be electronically designed such that one or more I/O ports can be used at the same time, for example allowing for simultaneous receipt of data from the patient monitor 2402 and the pulse oximeter 2406. In some embodiments, the patient monitor 2402 can send this monitored data to the breathing apparatus 2404 using wireless communication for example Bluetooth or Wi-Fi, or wired communication such as a Serial bus, LAN, USB, and/or other means of wired communication to send data in real time, with a small amount of lag such as 50 ms, and/or send previous data stored in patient monitor RAM or EEPROM for analysis by the breathing apparatus 2404. This lag time and sampling rate for data sent to the breathing apparatus 2404 can be fixed or variable, along with amount/time duration of data stored, can be determined based on the processing capabilities of the patient monitor 2402. A secure digital (SD) card or other non-volatile memory format may be used to store a patient profile of vital sign and/or breathing data from the breathing apparatus 2404, which can be analyzed separately either locally on a computer and/or using cloud software 2408 for use by a healthcare provider. The predictive breath detection software can be a cloud based software program 2408. The analysis and computations related to the pressure sensor 526 and other breathing sensor data is done in the cloud-based software 2408 using one or more control algorithms. The controller 504 inside the breathing apparatus 2404 receives a set of instructions from the cloud software 2408, such as but not limited to "OPEN Valve 1 at 00:03:07 time", "allow flow of 6 LPM of oxygen for 1.375 seconds", etc. The cloud-based software 2408 can communicate with the breathing apparatus 2404 using a variety of internet or communication protocols such as Wi-Fi, LAN, Wi-LAN, Bluetooth, 3G, 4G LTE, 5G, VPN, wireless hotspots, and/or other means. The breathing apparatus 2404 may have an integrated IoT device to allow low latency wireless communication with the cloud software 2408. The predictive breath detection software may be executed in the cloud-based software system 2408 and/or the internal controller 504 of the breathing apparatus 2404. As such, the cloud-based software system 2408 may only be used to store data, such as the data collected as described above with respect to the breathing apparatus 2404, the patient or vital sign monitor 2402 and/or the pulse oximeter 2046. In other words, the data collected may reside on the cloud-based software system 2408. To this end, the cloud-based software system 2408 may be in communication with the controller 504 of the breathing apparatus 2404, a patient or vital sign monitor 2402 and/or a pulse oximeter 2046. This collected data may include, among other things, readings 2202 as well as the time stamps shown in FIG. 4. The data stored on the cloud-based software system 2408 may then be communicated to the controller 504 of the breathing apparatus 2404. In this case, the control algorithm resides in the controller 504 of the breathing apparatus 1100. Therefore, the controller 504 of the breathing apparatus 2404 executes the control algorithm based on the data received from the cloud-based software system 2408. Alternatively, the cloud-based software 2408 not only stores the data collected as described above with respect to FIGS. 4 and 5, but also executes the analysis and computations required to predict breathing by the user and calculates, among other things, the flow rate of the output gas OG supplied to the user based on that analysis and computations. In other words, in this case, the cloud-based system 2408 stores the data collected and executes the control algorithm. In this case, the cloud-based software system 2408 communicates the flow rate of the output gas OG to the controller 504 of the breathing apparatus 2404. The controller 504 then commands the breathing apparatus 2404 to output the output gas OG at the flow rate determined by the cloud-based software system 2408. It is also envisioned that the data may reside in different devices, such as the controllers of a patient or vital sign monitor 2402 and/or the pulse oximeter 2406 and then communicated to the controller 504 of the breathing apparatus 2404. The controller 504 of the breathing apparatus 2404 may also store data relating to the pressure measurements of the pressure sensor 526.

Figure 8:
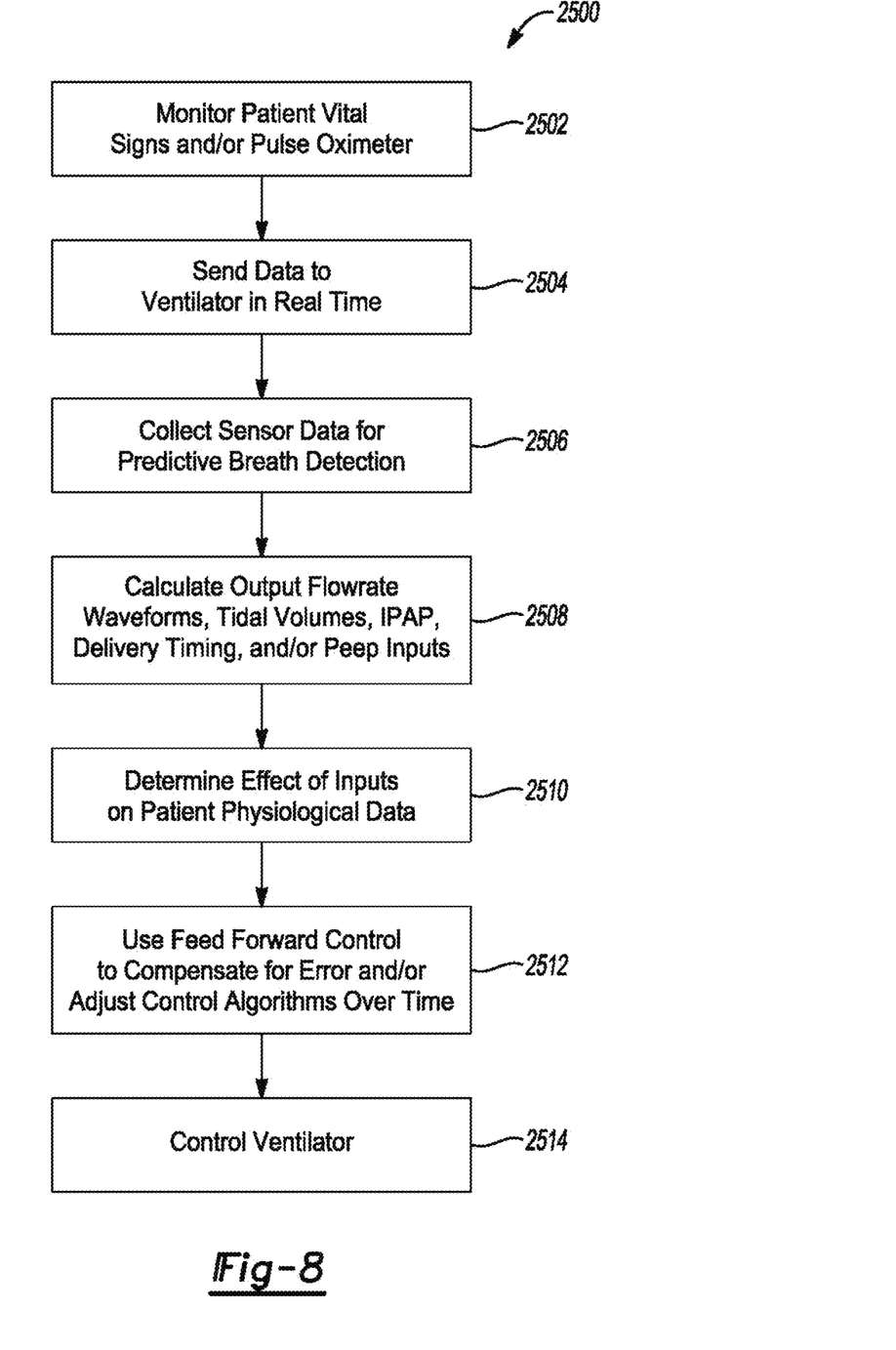
FIG. 8 is a flowchart of a method for dynamically adjusting tidal volumes of a breathing apparatus based on the $PaO_2$ saturations and vital sign monitor data.

The controller 504 and/or the cloud-based software system 2408 can include and/or be in communication with a memory and a database for receiving, storing and/or providing data from the pressure sensors 526, the pulse oximeter 2406, and/or the patient monitor 2402. In addition, the controller 504 and/or the cloud-based software system 2408 may include a central processing unit (not shown) for executing the method 2500. The memory of the controller 504 and/or the cloud-based software system 2408 may at least partially be tangible and non-transitory (e.g., ROM, RAM, EEPROM, etc.) and may be of a size and speed sufficient, for example, to execute the method 2500, storing the database, and/or communication with the breathing apparatus 2404, the controller 504, the pressure sensor 526, the pulse oximeter 2406, and/or the patient monitor 2406. The examples provided herein are non-limiting. For example, it would be understood that the functions of the cloud-based software system 2408 may be provided by a single server, or may be distributed among multiple servers, including third party servers, and that the data within the cloud-based software system 2408 may be provided by databases configured other than as described for the database. For example, the event duration data and/or process parameters related to breathing apparatus 2404 may reside in a shared database stored in the controller cloud-based system 2408 in communication with the server 20. The database may be distributed among multiple servers, including third party servers, in communication with each other and the server 20 through a network (not shown), such as the Internet, and/or directly.

FIG. 8 is a flowchart of a method 2500 for using the breathing apparatus 2404 that dynamically adjusts tidal volumes based on $PaO_2$ saturations and vital sign monitor data. The method 2500 begins at block 2502. At block 2502, the vital signals of the patient are monitored with the patient or vital sign monitor 2402. The patient or vital sign monitor 2402 then generates sensor sign data indicative of the monitored vital signs of the patient. Also at block 2502, the oxygen saturation or oxygen level in the blood of the patient is monitored using the pulse oximeter 2406. The pulse oximeter 2406 then generates sensor oxygen data indicative of the monitored oxygen saturation or oxygen level in the oxygen of the patient. It is envisioned that the vital signs and the oxygen saturation or oxygen level in the blood may be measured using integrated or separate devices such as vital sign monitors, patient monitors, pulse oximeters, $EtCO_2$ sensors, external or internal flow, pressure, and/or gas concentration sensors.

Then, the method 2500 proceeds to block 2504. At block 2504, the sensor sign data generated by the patient or vital sign monitor 2402 and the sensor oxygen data generated by the pulse oximeter 2406 is communicated to the controller 504 of the breathing apparatus 2404 in real time. The controller 504 of the breathing apparatus 2404 therefore receives the sensor sign data generated by the patient or vital sign monitor 2402 and the sensor oxygen data generated by the pulse oximeter 2406 in real time. Then, the method 2500 continues to block 2506.

At block 2506, the pressure sensor 526 measures and monitors the breathing pressures (e.g., nasopharynx pressure) of the patient. The pressure sensor 526 generate breathing sensor data indicative of the breathing pressure of the patient. This breathing sensor data is then communicated to the controller 504 of the breathing apparatus 2404. The controller 504 then collects the breathing sensor data generated by the pressure sensor 526 in real time. After collecting breathing sensor data, the method 2500 continues to block 2508.

At block 2508, the controller 504 of the breathing apparatus 2404 and/or the cloud-based software system 2408 uses the breathing sensor data to, among other things, predict breathing by the patient as discussed above with respect to FIG. 4. In addition, the controller 504 of the breathing apparatus 2404 calculates and/or predicts $O_2$ flow rate waveforms, tidal volumes, IPAP, delivery timing, inhalation/exhalation (IE) ratios, and/or PEEP inputs based on a variety of data measurements including but not limited to: predictive breath detection using pressure sensor measurements, breathing flow rate measurements, vital signs from a vital sign and/or patient monitor 2402 and/or pulse oximeter 2406, such as heart rate, blood pressure, and/or $SpO_2$, pulse oximetry data regarding arterial blood gases such as $SpO_2$, $SpCO_2$, $PaO_2$, $EtCO_2$, and/or $PaCO_2$, breathing gas concentration percentage of elements or compounds such as $O_2$ percentage, $N_2$ percentage, $CO_2$ percentage, and/or trace gases in ppm. After block 2508, the method 2500 proceeds to block 2510.

At block 2510, the controller 504 of the breathing apparatus 2404 and/or the cloud-based software system 2408 determines the effect of changing inputs, such as $O_2$ flow rates, on patient physiological data, such as $SpO_2$, $PaCO_2$, heart rate, blood pressure. After block 2510, the method 2500 proceeds to block 2512.

At block 2512, the controller 504 of the breathing apparatus 2404 and/or the cloud-based software system 2408 then uses feedforward control to compensate for error and/or adjust control algorithms over time. As a result, physicians or healthcare providers do not need to manually adjust ventilator controls, such as PEEP, IPAP, etc. The method 2500 then proceeds to block 2514.

At block 2514, the controller 504 commands the breathing apparatus 2404 to supply the output gas OG to the user at predetermined times based on the predicted breathing by the user. In other words, the controller 504 controls the breathing apparatus 2404 on a breath by breath basis based on the times for the next predicted inhalation. For instance, the controller 504 may command the valve 502 to open a certain amount of time (e.g., 2 milliseconds) before the next predicted inhalation of the user is about to occur. As a result, the control of the breathing apparatus 2404 takes into account the other steps of the method 2500, such as the feed forward compensation for errors and/or adjusts the output gas to be supplied to the user. Thus, the controller 504 is programmed to control the output gas OG supplied to the user based on the data collected, among other things, from the pressure sensor 526, the pulse oximeter 2406, and/or the patient or vital sign monitor 2402. This control of the output gas OG may include commanding the breathing apparatus 2404 to supply the output gas OG at a certain flow rate as calculated in block 2508 and corrected in block 2512.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware that enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

What is claimed is:

1. A cloud-based breath detection software and patient monitoring system, comprising:
    a breathing apparatus including a controller;
    a patient monitor configured to monitor a vital sign of a user of the breathing apparatus;
    a pulse oximeter configured to measure and monitor an oxygen saturation or oxygen levels in the blood of the user of the ventilator;
    a cloud-based software system in communication with the controller of the breathing apparatus, the pulse oximeter, and the patient monitor;
    wherein the breathing apparatus includes:
        a tubing configured to receive an input gas;
        a flow outlet airline in fluid communication with the tubing, wherein the flow outlet airline is configured to supply an output gas to a user;
        a breath detection airline, wherein the breath detection airline is configured to receive breathing gas from the user during exhalation by the user via the breath detection airline;
        a pressure sensor in direct fluid communication with the breath detection airline, wherein the pressure sensor is in communication with the controller of the breathing apparatus, the pressure sensor is configured to measure breathing pressure from the user, and the pressure sensor is in communication with the cloud-based software system through the controller of the breathing apparatus;
    wherein the cloud-based software system is configured to determine a flow rate of the output gas supplied to the user by the breathing apparatus on a breath by breath basis based on data from the pressure sensor, the pulse oximeter, and the patient monitor;
    wherein the cloud-based software system is configured to communicate the flow rate of the output gas to be supplied to the user to the controller; and
    wherein the controller is programmed to control the output gas supplied to the user based on the flow rate of the output gas determined by the cloud-based software system.

2. The system of claim 1, wherein the cloud-based software system stores data from the pressure sensor, the pulse oximeter, and the patient monitor.

3. The system of claim 2, wherein the cloud-based software system is programmed to predict inhalation by the user based on measurements from the pressure sensor.

4. The system of claim 3, wherein the cloud-based software system is programmed to time stamp the measurements from the pressure sensor in order to predict the inhalation by the user.

5. The system of claim 4, wherein the cloud-based software system is programmed to generate a breath pattern of the user based on the measurements from the pressure sensor, and the breath pattern is used to predict the inhalation by the user.

6. The system of claim 5, wherein the cloud-based software system is programmed to determine effects of the flow rate of the output gas on physiological data of the user collected by the pulse oximeter and the patient monitor.

7. The system of claim 6, wherein the cloud-based software system is programmed to use a feed forward control to adjust the output gas to be supplied to the user by the breathing apparatus.

* * * * *